United States Patent
El Kodadi et al.

(10) Patent No.: US 9,934,353 B2
(45) Date of Patent: Apr. 3, 2018

(54) FOCUS MEASUREMENTS USING SCATTEROMETRY METROLOGY

(71) Applicant: KLA-Tencor Corporation, Milipitas, CA (US)

(72) Inventors: Mohamed El Kodadi, Saint Martin D'Heres (FR); Nuriel Amir, St. Yokne'am (IL); Roie Volkovich, Hadera (IL); Vladimir Levinski, Migdal Haemek (IL); Yoel Feler, Haifa (IL); Daniel Kandel, Aseret (IL); Nadav Gutman, Zichron Ya'aqov (IL); Stilian Pandev, Santa Clara, CA (US); Dzimtry Sanko, Vallejo, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 32 days.

(21) Appl. No.: 14/974,732

(22) Filed: Dec. 18, 2015

(65) Prior Publication Data

US 2016/0103946 A1     Apr. 14, 2016

Related U.S. Application Data

(63) Continuation of application No. PCT/US2015/023405, filed on Mar. 30, 2015.
(Continued)

(51) Int. Cl.
*G06F 17/50* (2006.01)
*G03F 7/20* (2006.01)
*G01N 21/47* (2006.01)

(52) U.S. Cl.
CPC ..... *G06F 17/5081* (2013.01); *G01N 21/4785* (2013.01); *G03F 7/70641* (2013.01); *G03F 7/70683* (2013.01); *G06F 17/5072* (2013.01)

(58) Field of Classification Search
USPC .......................................... 716/54
See application file for complete search history.

(56) References Cited

U.S. PATENT DOCUMENTS

2003/0123052 A1   7/2003  Ausschnitt et al.
2003/0160163 A1*  8/2003  Wong ..................... G02B 27/46
                                                250/237 R
(Continued)

FOREIGN PATENT DOCUMENTS

WO        2010076232 A2     7/2010

OTHER PUBLICATIONS

Wong, C. et al. "CD optimization methodology for extending optical lithography," Proc. of SPIE vol. 8681, 868137 • © 2013 SPIE.
(Continued)

*Primary Examiner* — Eric Lee
(74) *Attorney, Agent, or Firm* — Suiter Swantz pc llo (57) ABSTRACT

Target designs and methods are provided, which relate to periodic structures having elements recurring with a first pitch in a first direction. The elements are periodic with a second pitch along a second direction that is perpendicular to the first direction and are characterized in the second direction by alternating, focus-sensitive and focus-insensitive patterns with the second pitch. In the produced targets, the first pitch may be about the device pitch and the second pitch may be several times larger. The first, focus-insensitive pattern may be produced to yield a first critical dimension and the second, focus-sensitive pattern may be produced to yield a second critical dimension that may be equal to the first critical dimension only when specified focus requirements are satisfied, or provide scatterometry measurements of zeroth as well as first diffraction orders, based on the longer pitch along the perpendicular direction.

22 Claims, 9 Drawing Sheets

Related U.S. Application Data

(60) Provisional application No. 61/973,151, filed on Mar. 31, 2014.

(56) References Cited

U.S. PATENT DOCUMENTS

| | | |
|---|---|---|
| 2004/0070771 A1 | 4/2004 | Ausschnitt |
| 2006/0132744 A1* | 6/2006 | Hauschild ............ G03F 7/70641 355/55 |
| 2006/0215161 A1 | 9/2006 | Den Boef et al. |
| 2010/0177312 A1 | 7/2010 | Fujimori et al. |
| 2014/0141536 A1 | 5/2014 | Levinski et al. |

OTHER PUBLICATIONS

Spaziani, Nicolas et al. "Lithography process control using in-line metrology," Proc. of SPIE vol. 8324, 83241L • © 2012 SPIE.
Brunner, T.A. and C. P. Ausschnitt, "Process Monitor Gratings", Proc. of SPIE vol. 6518-2 © 2007 SPIE.

\* cited by examiner

FOCUS MEASUREMENTS USING SCATTEROMETRY METROLOGY

CROSS REFERENCE TO RELATED APPLICATIONS

This application is filed under 35 U.S.C. § 111(a) and § 365(c) as a continuation of International Patent Application No. PCT/US2015/023405, filed Mar. 30, 2015, which application claims the benefit of U.S. Provisional Patent Application No. 61/973,151 filed on Mar. 31, 2014, which applications are incorporated herein by reference in their entirety.

BACKGROUND OF THE INVENTION

1. Technical Field

The present invention relates to the field of metrology, and more particularly, to focus measurements using scatterometry metrology.

2. Discussion of Related Art

The lithographic tool is a machine that is used to print a desired pattern onto substrate. The tool is used to transfer a pattern from a mask to an individual layer of the integrated circuit, printed on a wafer. The transfer is typically carried out via imaging onto a sensitive layer, termed the resist. As the targeted critical dimension (CD) of the pattern elements shrinks, the imaging process window shrinks, which results in a smaller process window in terms of depth of focus (DOF). In order to control the printed pattern uniformity, it is necessary to measure the parameters of the lithographic tool and especially the parameters of the focus. For example, the advanced node requires very tight focus control, e.g., $3\sigma<10$ nm across the wafer.

Wong et al. 2013 ("CD optimization methodology for extending optical lithography" in Proc. of SPIE Vol. 8681, 868137), the article being incorporated herein by reference in its entirety, teach using, for focus measurements, asymmetric targets for which the asymmetry, i.e., the difference between the effective side wall angles (SWA) at the left and the right edges, changes monotonically through focus (see reference 1). The SWA difference shows up as an intensity difference between +1 and −1 diffractions orders in the measured scatterometry signal. However, the target pitch taught by Wong et al. is at least four times the product pitch, which makes the target sensitive to lithographic tool aberration. Another issue is that when the SWA angle asymmetry is small the signal difference becomes small, leading to inaccurate results.

Spaziani et al. 2012 ("Lithography process control using in-line metrology" in Proc. of SPIE Vol. 8324, 83241L) and Brunner and Ausschnitt 2007 ("Process Monitor Gratings" in Proc. of SPIE Vol. 6518-2), the articles being incorporated herein by reference in their entirety, teach using, for focus measurements, Focus Dose Pattern and Process Monitor Grating, in which targets are designed for higher sensitivity to dose and focus variation. The targets are made more sensitive by using scattering bar techniques, end of line techniques, and forbidden pitch. However, the targets are disadvantageous with respect to their small depth of field (DOF) and the printability of the patterns in a whole range of process window. The measurement method uses the scatterometry model base approach which makes it sensitive to model errors.

U.S. Patent Publication No. 20140141536, which is incorporated herein by reference in its entirety, discloses a segmented mask including a set of cell structures. Each cell structure includes a set of features having an unresolvable segmentation pitch along a first direction. The unresolvable segmentation pitch along the first direction is smaller than the illumination of the lithography printing tool. The cell structures have a pitch along a second direction perpendicular to the first direction. The unresolvable segmentation pitch is suitable for generating a printed pattern for shifting the best focus position of the lithography tool by a selected amount to achieve a selected level of focus sensitivity.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a target design comprising a target design comprising a periodic structure having a plurality of recurring elements characterized by a first pitch in a first direction, wherein the elements are periodic with a second pitch along a second direction that is perpendicular to the first direction and are characterized in the second direction by alternating, focus-sensitive and focus-insensitive patterns with the second pitch.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Prior to the detailed description being set forth, it may be helpful to set forth definitions of certain terms that will be used hereinafter.

The term "focus-insensitive pattern" as used in this application refers to a region of an element in a target design which is continuous and not subdivided, and is characterized by a uniform critical dimension. The term "focus-sensitive pattern" as used in this application refers to a region of an element in a target design which is either subdivided (in any direction, e.g., segmented or including gaps) and/or is characterized by a non-uniform critical dimension.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
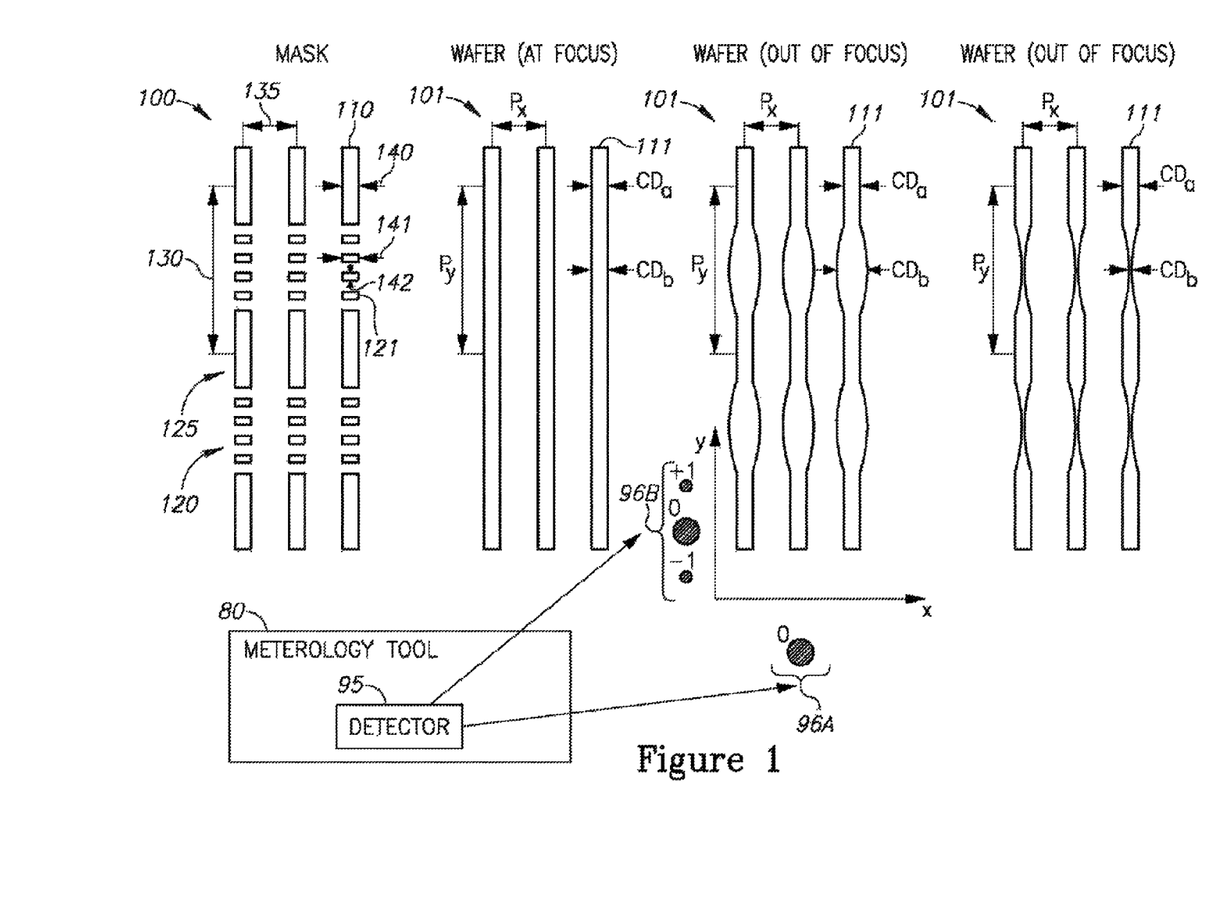
FIG. 1 is a level schematic illustration of target designs on the mask, produced targets and scatterometry measurements thereof, according to some embodiments of the invention.

FIG. 1 is a level schematic illustration of target designs 100 on the mask, produced targets 101 and scatterometry measurements 96A, 96B thereof, according to some embodiments of the invention.

Target designs 100 comprise a periodic structure having a plurality of recurring elements 110 characterized by a first pitch 135 in a first direction (x). Elements 110 are themselves periodic with a second pitch 130 along a second direction (y) that is perpendicular to the first direction. Elements 110 are characterized in the second direction by alternating, focus-sensitive and focus-insensitive patterns 120, 125, respectively, with second pitch 130. Focus-insensitive pattern 125 may have a first critical dimension ($CD_a$) upon production from an elements width 140 on the mask. Focus-sensitive pattern 125 may exhibit a second critical dimension ($CD_b$) upon printing from the mask. In certain embodiments, second critical dimension $CD_b$ depends upon the focus during production of target 101. In certain embodiments, second critical dimension $CD_b$ may equal first critical dimension $CD_a$ upon production on the wafer only when specified focus requirements are satisfied.

Produced target 101, with produced elements 111, is characterized by a pitch $P_x$ in the first direction (x) and possibly a pitch $P_y$ in the second direction (y), in case $CD_b$ differs from $CD_a$ (illustrated in an exaggerated manner). Pitch $P_y$ may be designed to be several time larger than pitch $P_x$ (which may be similar to device pitch) and enable scatterometry measurements of the ±first diffraction orders in addition to the zeroth diffraction order (96B) by a metrology tool 80. The scatterometry measurements may thus be used to estimate the focus with which targets 101 were produced.

FIGS. 2A-2F are high level schematic illustrations of target designs 100, according to some embodiments of the invention. FIGS. 2A-2F represent target designs 100 on a respective photolithography mask used to produce targets 101 on the wafer. It is noted that, as explained above, the actual produced form 101 of target designs 100 on the wafer may differ from target designs 100 on the mask depending on production parameters such as focus and dose. FIGS. 2A-2F schematically illustrate non-limiting possibilities of target designs 100, which may be modified according to the principles which are presented below.

Target designs 100 may comprise a periodic structure having a plurality of recurring elements 110 characterized by first pitch 135 in a first direction (x), which are also periodic with second pitch 130 along a second direction (y) that is perpendicular to the first direction. Elements 110 may be characterized in the second direction by alternating, focus-sensitive patterns 120 and focus-insensitive patterns 125, which alternate with second pitch 130.

In certain embodiments, upon production, first, focus-insensitive pattern 125 may have a first critical dimension marked $CD_a$, and second, focus-sensitive pattern 120 may have a second critical dimension marked $CD_b$. In certain embodiments, the latter, focus-sensitive pattern 120 may exhibit the first critical dimension ($CD_a$) upon production on a wafer only when specified focus requirements are satisfied. Upon inappropriate focus a different critical dimension, e.g., between $CD_b$ and $CD_a$ may be produced.

In certain embodiments, first pitch 135 may be produced to yield $P_x$ that is close to a product pitch and the produced first critical dimension ($CD_a$) may be less than half the produced pitch $P_x$. In certain embodiments, second pitch 130 may be produced to yield $P_y$ that may be 1½-2 times the first critical dimension ($CD_a$). In certain embodiments, the second critical dimension ($CD_b$) may be ½-1 times the first critical dimension ($CD_a$). In certain embodiments, $P_y$ may be 4-6 times $P_x$. In certain embodiments, target design 100 may be configured to produce $P_x$ that yields a zeroth diffraction order signal 96A and produce $P_y$ that yields zeroth as well as ±first diffraction order signals 96B upon scatterometry measurements.

In certain embodiments, second, focus-sensitive pattern 120 may be segmented at a sub-resolution pitch. Focus-sensitive pattern 120 may be designed in different ways, some of which are illustrated in FIG. 2A-2F. For example, focus-sensitive pattern 120 may comprise horizontal element(s) 121 and/or vertical element(s) 122. The term "horizontal" in this context is understood to be along the x direction (i.e., along first pitch 135 and respectively along the short dimension of element 110) while the term "vertical" in this context is understood to be along the y direction (i.e., along second pitch 130 and respectively along the long dimension of element 110). Either horizontal element(s) 121 or vertical element(s) 122 alone may define focus-sensitive pattern 120 (see e.g., FIGS. 2A, 2F) or horizontal element(s) 121 and vertical element(s) 122 may be combined to form focus-sensitive pattern 120 (FIGS. 2B-2E).

Figure 2A:
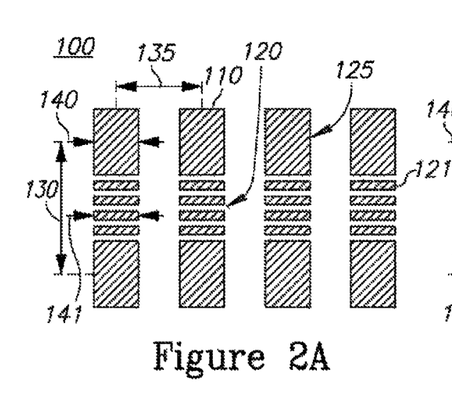
FIGS. 2A-2F are high level schematic illustrations of target designs, according to some embodiments of the invention.
Figure 2B:
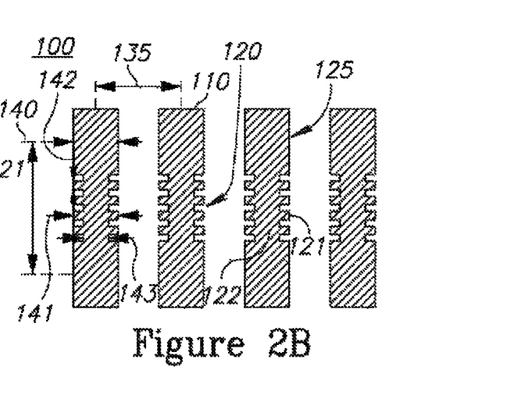
Figures 2C, 2D:
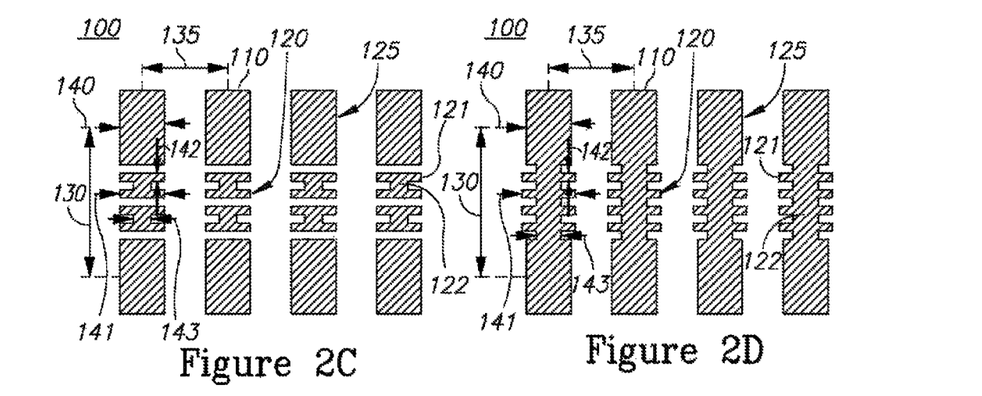
Figures 2E, 2F:
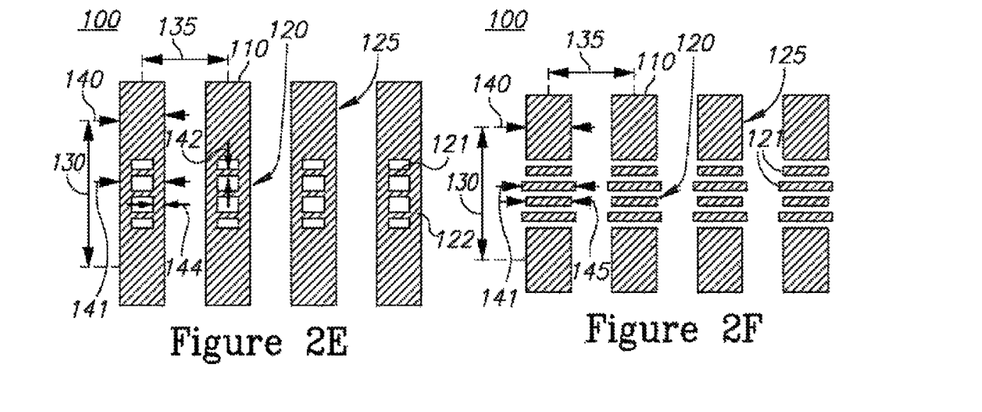

Horizontal element(s) 121 and/or vertical element(s) 122 may be periodic (FIGS. 2A-2F for horizontal element(s) 121, though horizontal element(s) 121 does not necessarily have to be periodic; and FIGS. 2C, 2E for vertical element(s) 122 with differing directions of periodicity) and may vary in length within focus-sensitive pattern 120 (e.g., FIG. 2F). The dimensions of sub-resolution elements 121, 122 may be optimized according to production and measurements tools and parameters as well as according to required focus sensitivity. Exemplary feature dimensions comprise lengths 141, 145 and width 142 of horizontal elements 121, length (not designated) and widths 143, 144 of vertical elements 122, depending on the specific designs.

Lithographic tool focus offset may be measured using target designs 100. Target designs 100 may be configured to be robust, sensitive to focus, and correlate to product. The measurement approach may be configured to use zeroth and first diffraction order signals or parts thereof (e.g., +1 and/or −1 orders). The pitch of produced target designs 100 ($P_x$) and/or the critical dimension of produced target designs 100 ($CD_a$) may be close to product pitch. In a non-limiting manner, line patterns are used to illustrate target designs 100, and $CD_a$ is illustrated to be about or less than half $P_x$. In certain embodiments, $CD_a$ may be close to the product CD and/or may be e.g., 30% to 70% of $P_x$.

The enhanced sensitivity of produced targets 101 to focus parameters may be achieved along a direction that is different from the main measurement direction (along which $P_x$ is designed), typically a direction perpendicular thereto. Thus, along that direction, a secondary pitch $P_y$ is formed by producing alternating patterns 120, 125 along element 110. It is noted that while only one focus-sensitive pattern 120 is illustrated in FIGS. 2A-2F, multiple alterations and multiple focus-sensitive patterns 120 may be designed along element 110, depending on its length. Some or all elements 110 in target design 100 may comprise alternating focus-sensitive and focus-insensitive patterns 120, 125 (respectively), and different elements 110 may comprise different pattern 120 and/or 125, yielding different pitches $P_y$ and/or different critical dimensions $CD_b$.

In certain embodiments, secondary pitch 130 may be larger than first pitch 135, e.g., up to four to six times larger, and be, for example between 400-1200 nm. The first critical dimension ($CD_a$) may be close to product CD and may be e.g., 30% to 70% of $P_x$ The second critical dimension ($CD_b$) may be e.g., 30% to 70% of $P_y$.

Second, focus-sensitive pattern 120 may be patterned by sub-resolution features 121, 122, i.e., features which are not necessarily reproduced in produced target 101, yet influence the critical dimension of the respective part of produced element 111. Target design 100 may hence be printed as a periodic structure lacking the distinction between first and second patterns 120, 125, at least in cases of correct photolithographic parameters such as focus and dose, and may indicate, by deviation from such expected periodic structure, the use of inappropriate photolithographic parameters such as focus and dose, e.g., parameters beyond specified tolerance regions. The details of focus-sensitive pattern 120 may be used and designed to define and adjust the sensitivity region and tolerance regions.

In certain embodiments, focus-sensitive and focus-insensitive patterns 120, 125 may have similar sensitivity to dose changes while patterns 120, 125 may differ in their focus sensitivity, i.e., under dose changes $CD_b$ may stay approximately equal to $CD_a$, while under focus changes $CD_b$ may diverge from $CD_a$, depending on the extent of the focus deviation. In certain embodiments, a uniformity of elements 111 or a symmetry between produced patterns 120, 125 within elements 111 may serve as a metric for estimating the focus deviation, or the focus correctness.

Figure 3A:
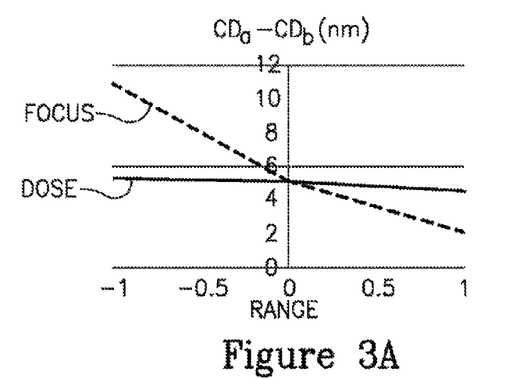
FIGS. 3A-3C schematically illustrate simulation results for producing elements 110, according to some embodiments of the invention.
Figure 3B:
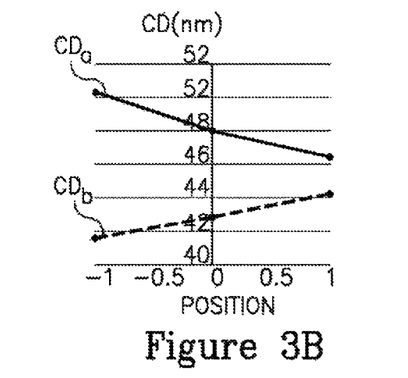
Figure 3C:
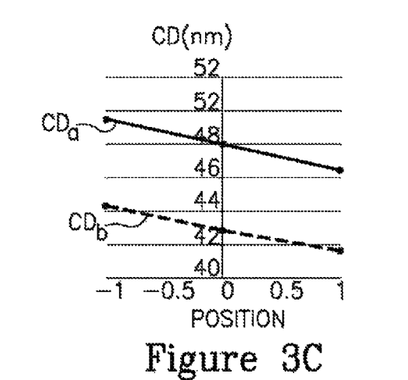

FIGS. 3A-3C schematically illustrate simulation results for producing elements 110, according to some embodiments of the invention. Using PROLITH as the simulation tool, FIG. 3A illustrates the dependency of $CD_a$-$CD_b$ of resist structures 111 produced by the illustrated target design 100 (similar to FIG. 2B) on focus changes having the values −60 nm, 0 and +60 nm and on dose changes having the values −1 mJ/cm², 0, +1 mJ/cm². FIGS. 3B and 3C depict the results for each $CD_a$, $CD_b$, for focus changes (FIG. 3B) and dose changes (FIG. 3C). In the illustrated embodiments, $CD_b$ is not equal to $CD_a$, and the difference $CD_a$-$CD_b$ clearly depends on, and hence may be used to indicate focus deviations. It is noted that $CD_a$ and $CD_b$ depend on the dose in a similar manner and thus the focus parameter may be measured independently of the dose parameter.

Figure 4:
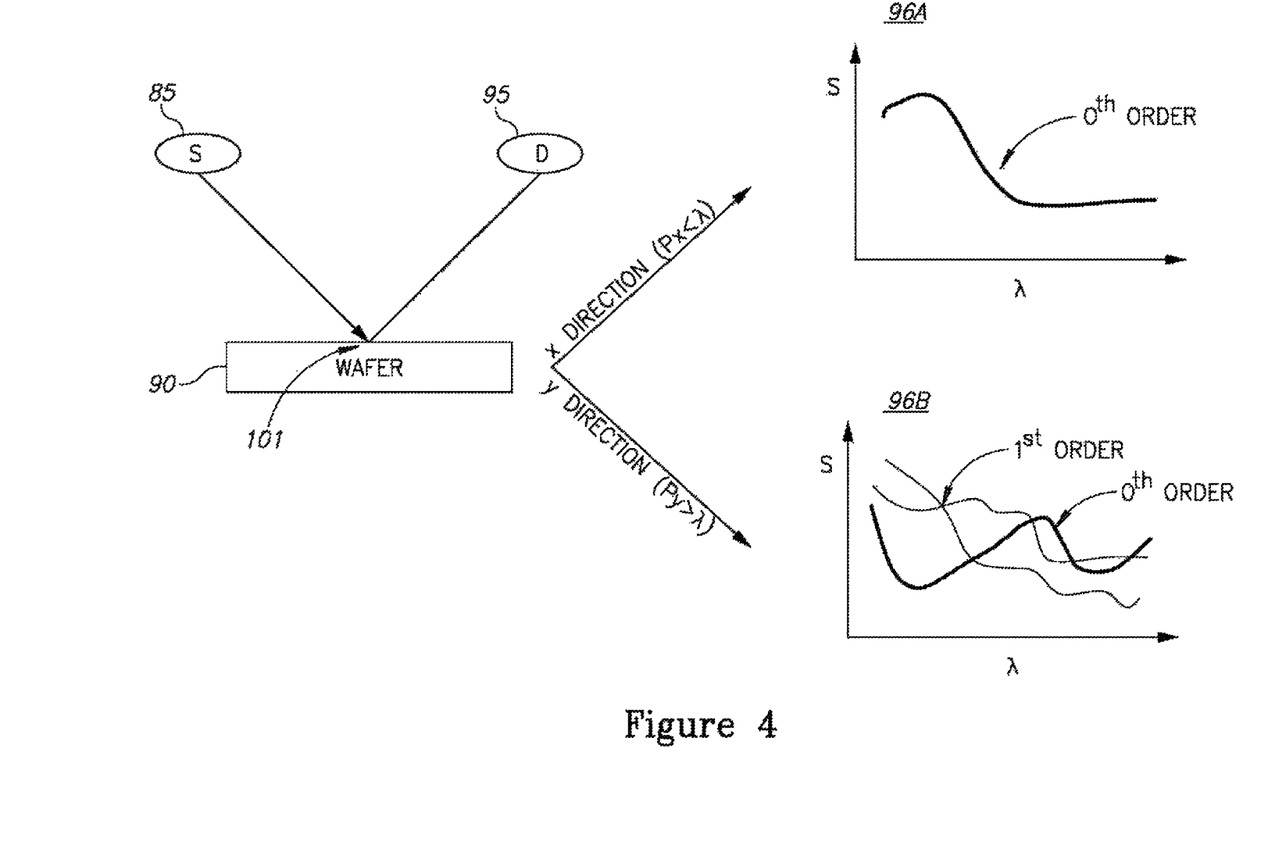
FIG. 4 is a high level schematic illustration of measuring the focus using targets on a wafer, produced using target designs, according to some embodiments of the invention.

FIG. 4 is a high level schematic illustration of measuring the focus using targets 101 on wafer 90 produced using target designs 100, according to some embodiments of the invention. An illumination source 85 is used to derive diffraction signals 95 from target 101. Diffraction signals 95 are schematically illustrated on the right hand side of FIG. 4, showing the zeroth order signal as function of wavelengths (along the x direction) 96A and both zeroth and ±first diffraction orders signal along the y direction 96B.

Figure 5A:
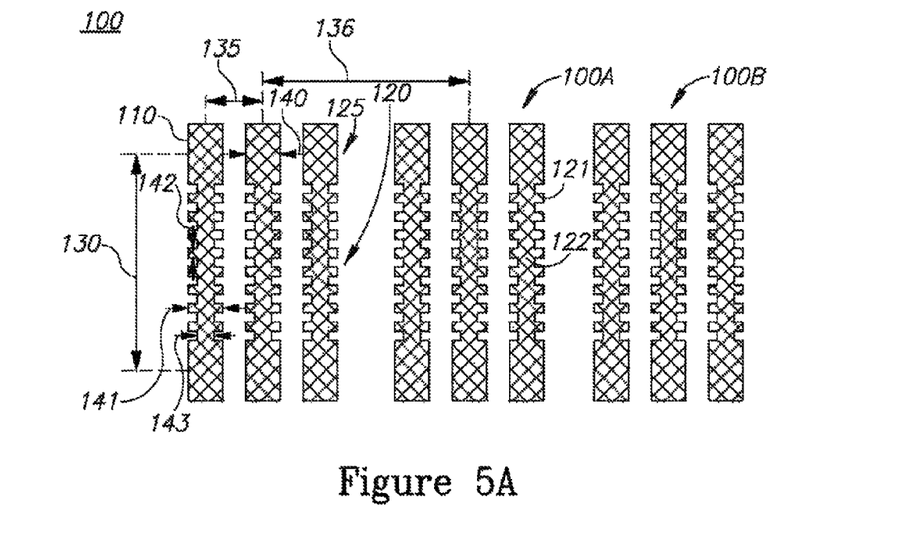
FIGS. 5A and 5B are high level schematic illustrations of target designs, according to some embodiments of the invention.
Figure 5B:
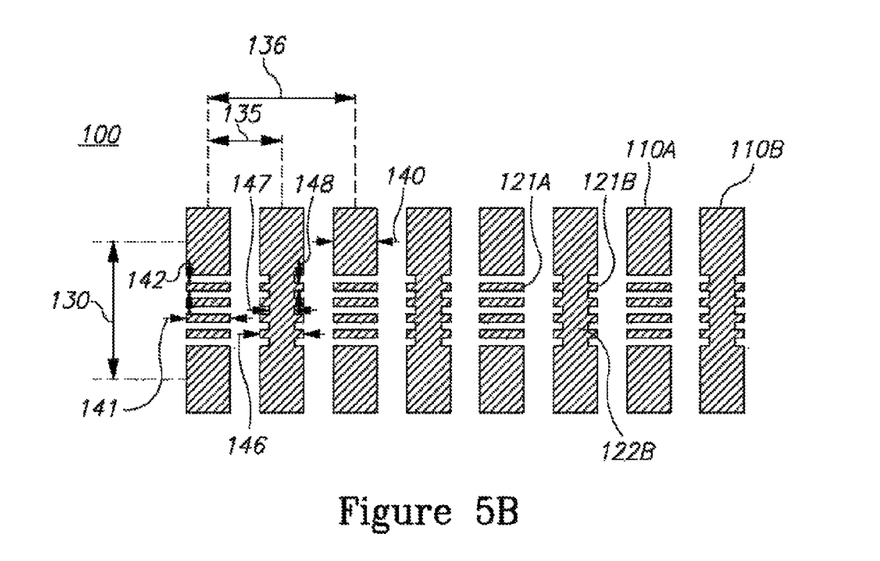

FIGS. 5A and 5B are high level schematic illustrations of target designs 100, according to some embodiments of the invention. Certain embodiments comprise target designs 100 having multiple sub-targets 100A, 100B comprising similar elements 110 and separated into distinct groups at a pitch 136 which is different from first pitch 135 (FIG. 5A). Certain embodiments comprise target designs 100 having two or more types of elements 110, e.g., elements 110A, 110B with different focus-sensitive patterns 120. In a non-limiting example, illustrated in FIG. 5B, elements 110A, 110B are of the types presented in FIGS. 2A, 2B, respectively, composed of horizontal elements 121A in the former and of horizontal elements 121B and vertical elements 122B in the latter. Target designs 100 are hence characterized by two distinct horizontal pitches, pitch 135 between adjacent elements 110A, 110B and another pitch 136 (=2·pitch 135) between adjacent similar elements 110A (or similar elements 110B). The difference between focus-sensitive patterns 120 in elements 110A, 110B may be used to enhance the accuracy of the focus measurements derived therefrom. Exemplary feature dimensions comprise lengths 141, 146 and widths 142, 148 of horizontal elements 121, 121A, 121B, length (not designated) and widths 143, 147 of vertical elements 122, 122B depending on the specific designs.

Figure 6A:
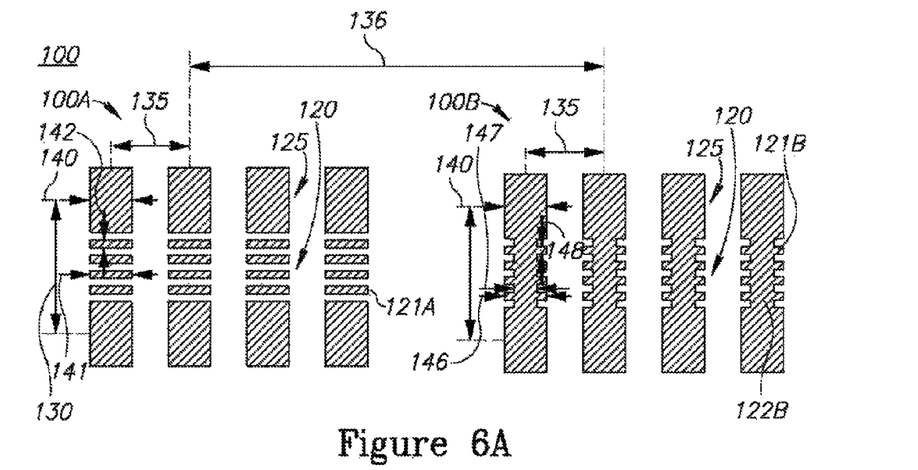
FIGS. 6A-6C are high level schematic illustration of target designs, according to some embodiments of the invention.
Figure 6B:
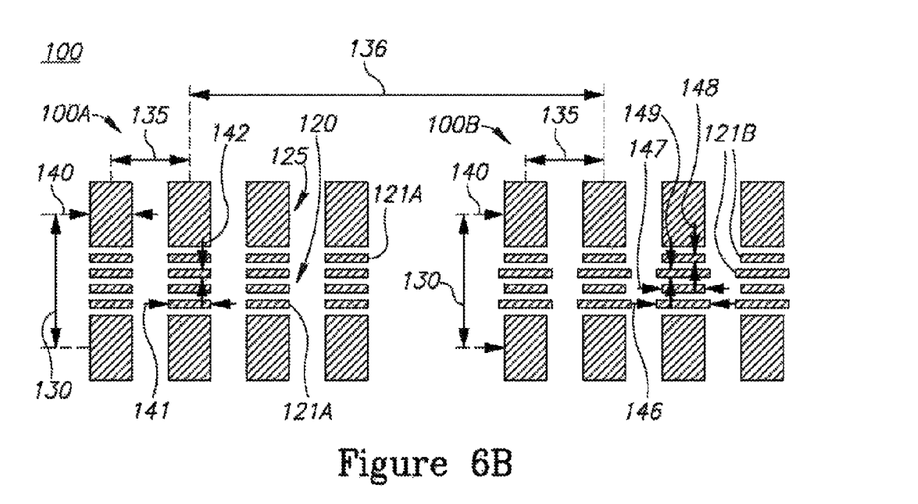
Figure 6C:
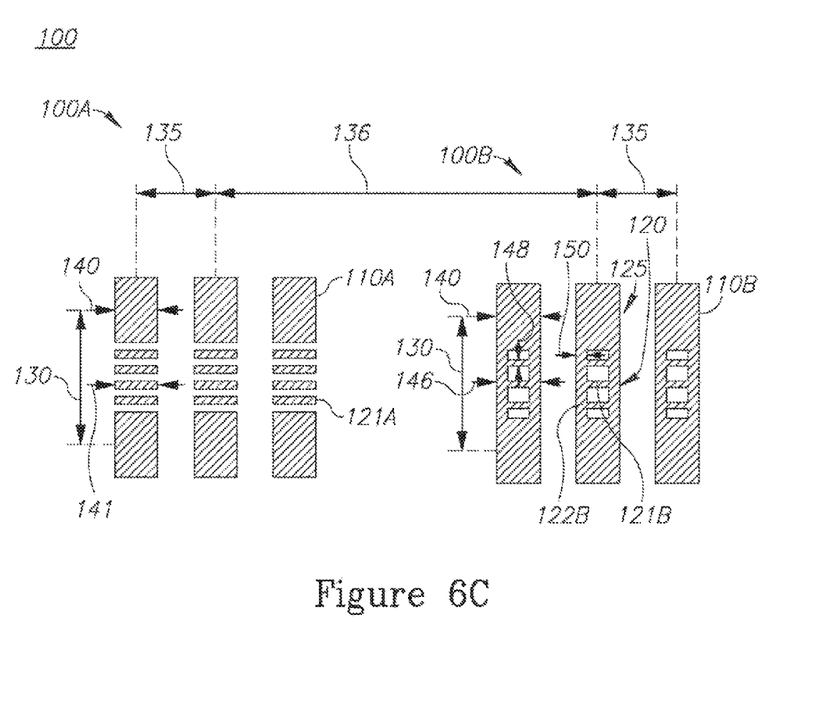

Certain embodiments comprise target designs 100 having two or more sub-targets 100A, 100B with elements 110 that differ in their focus-sensitive patterns 120. Using multiple focus sensitive patterns 120 enhances the accuracy of the focus measurements derived therefrom. FIGS. 6A-6C are high level schematic illustrations of target designs 100, according to some embodiments of the invention. In the non-limiting examples, sub-target 100A is similar in the three designs to FIG. 2A (with horizontal elements 121A), while sub-target 100B is modified according to patterns introduced in FIGS. 2B, 2F and 2E, respectively (with horizontal elements 121B and vertical elements 122 in FIGS. 6A and 6C). Any combination of two or more sub-target designs may be used as target design 100. In the illustrated cases, sub-targets 100A, 100B are characterized by first pitch 135 while sub-targets 100A, 100B are designed at a larger pitch 136. Exemplary feature dimensions comprise lengths 141, 146 and widths 142, 148, 149 of horizontal elements 121A, 121B, length (not designated) and widths 147, 150 of vertical elements 122, depending on the specific designs.

Figure 7:
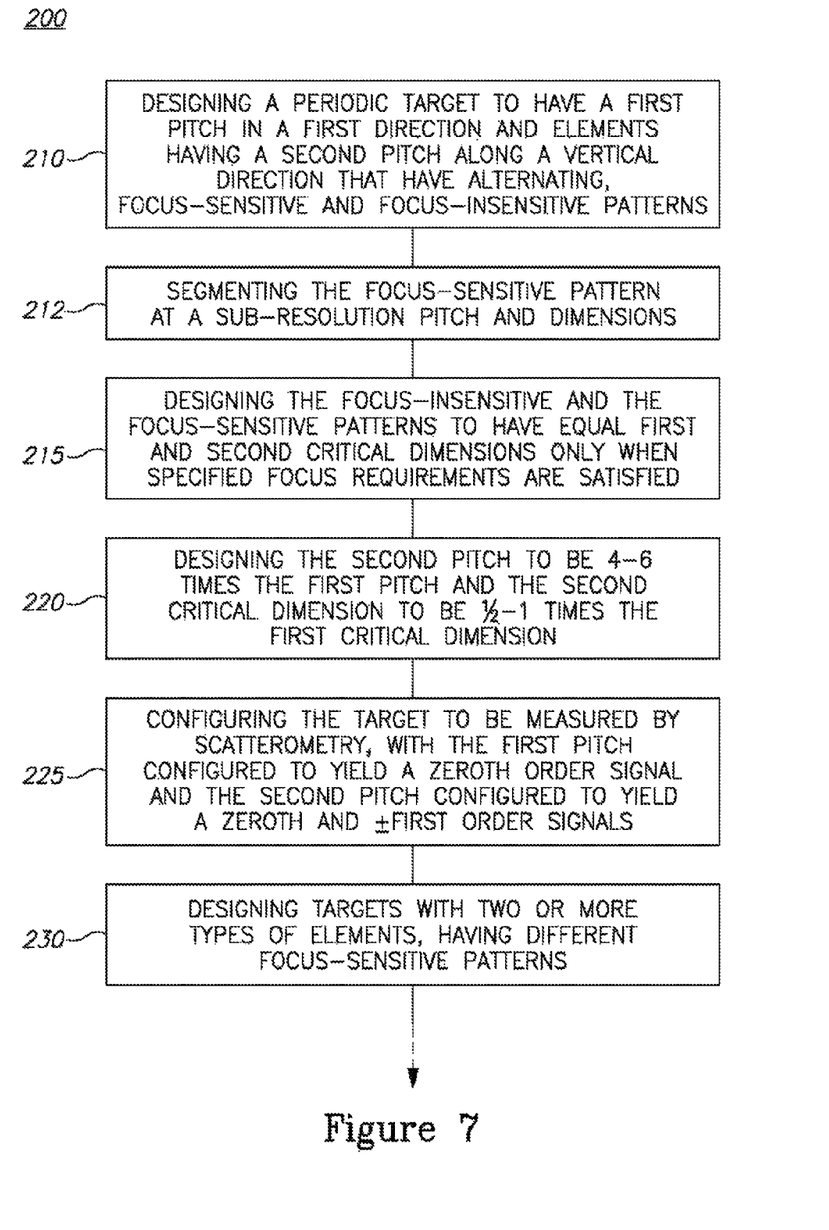
FIG. 7 is a high level flowchart illustrating a method, according to some embodiments of the invention.

FIG. 7 is a high level flowchart illustrating a method 200, according to some embodiments of the invention. Design stages in method 200 may be carried out at least partially by a computer processor.

Method 200 may comprise designing a periodic target to have a first pitch in a first direction and elements having a second pitch along a perpendicular direction that have alternating, focus-sensitive and focus-insensitive patterns (stage 210). In certain embodiments, method 200 may comprise segmenting the focus-sensitive pattern at a sub-resolution pitch (stage 212).

Method 200 may further comprise designing the focus-insensitive pattern to have upon production a first critical dimension, and the focus-sensitive pattern to have upon production a second critical dimension that equals the first critical dimension only when specified focus requirements are satisfied (stage 215).

For example, method 200 may comprise designing the second pitch to be 4-6 times the first pitch and the second critical dimension to be ½-1 times the first critical dimension (stage 220).

Method 200 may comprise configuring the target to be measured by scatterometry, wherein the first pitch is configured to yield zeroth order signal and the second pitch is configured to yield zeroth and at least one first order signals (stage 225).

Method 200 may comprise producing the designed target (stage 230) and verifying a tool's focus by measuring the produced focus-sensitive patterns (stage 240).

Method 200 may further comprise preparing a FEM (focus exposure matrix) wafer from the designed targets with varying critical dimensions and/or pitches (stage 250) and deriving a focus parameter from a comparison of a measured target signal with signals measured from the FEM wafer (stage 255).

Method 200 may further comprise deriving a model from scatterometry measurements of designed targets with varying critical dimensions and/or pitches (stage 260) and deriving a focus parameter from a measured target signal according to the model (stage 265). The model may be derived by the methods described in U.S. Patent Application No. 2013/0110477, disclosing process variation-based model optimizations for metrology, which is incorporated herein by reference in its entirety.

Advantageously, target designs 100 and methods 200 provide both higher sensitivity to scanner focus than the prior art as well as good target printability. Relations between CD variation, scatterometry signal parameters and focus are used to derive focus deviations. In certain embodiments, produced targets 101 are periodic with a main pitch ($P_x$) close to a product pitch and comprise a perpendicular structure having at least one repeating focus-sensitive pattern having a pitch $P_y$ larger than the illumination wavelength used by the scatterometer tool. Target designs 100 may comprise two or more sub-targets having different focus sensitivities. A signal model or reference targets may be used to derive the focus from respective diffraction signals (e.g., zeroth, +first and/or −first orders). Multiple targets or sub-targets may be used to de-correlate focus and dose measurements and/or deviations.

In certain embodiments, film pad targets may be used for under layer de-correlation. The diffraction order signal (e.g., zeroth order) may be extracted from measurements of the film pad target. The signal measured using the film pad target may be fed-forward to the measurement on the grating with the sensitive focus target, described above. In certain embodiments, under layer de-correlation using film pad targets may increase the accuracy of the focus measurement.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A target design comprising:
a plurality of structures including a plurality of elements, wherein the plurality of structures are arranged based on a first pitch in a first direction along a first axis, wherein the plurality of elements are arranged based on a second pitch in a second direction along a second axis substantially perpendicular to the first axis,
wherein the plurality of elements includes a plurality of focus-insensitive elements arranged in a focus-insensitive pattern, wherein the second pitch includes a spatial distance between adjacent focus-insensitive elements of the plurality of focus-insensitive elements,
wherein the plurality of elements includes a plurality of focus-sensitive elements arranged in a focus-sensitive pattern, wherein a set of the plurality of focus-sensitive elements is positioned between adjacent focus-insensitive elements of the plurality of focus-insensitive elements,
wherein the set of the plurality of focus-sensitive elements positioned between adjacent focus-insensitive elements of the plurality of focus-insensitive elements are arranged based on a third pitch, wherein the third pitch includes a spatial distance smaller than the spatial distance of the second pitch.

2. The target design of claim 1, wherein the focus-insensitive pattern includes a first critical dimension for the plurality of focus-insensitive elements, wherein the focus-sensitive pattern includes a second critical dimension for the plurality of focus-sensitive elements.

3. The target design of claim 2, wherein the second critical dimension is ½-1 times the first critical dimension.

4. The target design of claim 2, wherein the second critical dimension is not substantially similar to the first critical dimension if a selected set of focus requirements are not met.

5. The target design of claim 2, wherein the second critical dimension is substantially similar to the first critical dimension if a selected set of focus requirements are met.

6. The target design of claim 1, wherein the first pitch is substantially similar to a selected product pitch.

7. The target design of claim 1, wherein the second pitch is 4-6 times the first pitch.

8. The target design of claim 1, wherein the second pitch is larger than an illumination wavelength used by a lithography tool, wherein the third pitch is smaller than the illumination wavelength used by the lithography tool.

9. The target design of claim 1, wherein the target design is measured via scatterometry, wherein measuring the first pitch of the target design yields a zeroth-order diffraction signal, wherein measuring the second pitch of the target design yields at least one of a zeroth-order diffraction signal, a positive-first-order diffraction signal, or a negative first-order diffraction signal.

10. The target design of claim 1, wherein the plurality of focus-sensitive elements include one or more horizontal focus-sensitive elements with a long center axis substantially parallel to the first axis.

11. The target design of claim 1, wherein the plurality of focus-sensitive elements include one or more vertical focus-sensitive elements with a long center axis substantially parallel to the second axis.

12. The target design of claim 1, wherein the plurality of focus-sensitive elements include one or more horizontal focus-sensitive elements with a long center axis substantially parallel to the first axis and one or more vertical focus-sensitive elements with a long center axis substantially parallel to the second axis.

13. A method comprising:
generating a target design, wherein the target design includes a plurality of structures including a plurality of elements, wherein the plurality of structures are arranged based on a first pitch in a first direction along a first axis, wherein the plurality of elements are arranged based on a second pitch in a second direction along a second axis substantially perpendicular to the first axis,
wherein the plurality of elements includes a plurality of focus-insensitive elements arranged in a focus-insensitive pattern, wherein the second pitch includes a spatial distance between adjacent focus-insensitive elements of the plurality of focus-insensitive elements,
wherein the plurality of elements includes a plurality of focus-sensitive elements arranged in a focus-sensitive pattern, wherein a set of the plurality of focus-sensitive elements is positioned between adjacent focus-insensitive elements of the plurality of focus-insensitive elements,
wherein the set of the plurality of focus-sensitive elements positioned between adjacent focus-insensitive elements of the plurality of focus-insensitive elements are arranged based on a third pitch, wherein the third pitch includes a spatial distance smaller than the spatial distance of the second pitch; and
verifying a focus of a lithography tool by measuring the focus-sensitive pattern.

14. The method of claim 13, wherein the focus-insensitive pattern includes a first critical dimension for the plurality of focus-insensitive elements, wherein the focus-sensitive pattern includes a second critical dimension for the plurality of focus-sensitive elements.

15. The method of claim 14, wherein the second pitch is 4-6 times the first pitch, wherein the second critical dimension is ½-1 times the first critical dimension.

16. The method of claim 13, wherein the target design is measured via scatterometry, wherein measuring the first pitch of the target design yields a zeroth-order diffraction signal, wherein measuring the second pitch of the target design yields at least one of a zeroth-order diffraction signal, a positive-first-order diffraction signal, or a negative first-order diffraction signal.

17. The method of claim 13, further comprising
fabricating a focus and exposure matrix (FEM) wafer from the generated target design, wherein the FEM wafer includes at least one of a selected critical dimension or pitch.

18. The method of claim 17, further comprising:
deriving a focus parameter from a comparison of a measured target signal with a plurality of signals measured from the FEM wafer.

19. The method of claim 13, further comprising:
deriving a model from one or more scatterometry measurements of a plurality of target designs, wherein the plurality of target designs include at least one of one or more different critical dimensions or one or more different pitches.

20. The method of claim 19, further comprising:
deriving a focus parameter from a measured target signal according to the derived model.

21. The method of claim 13, wherein the second pitch is larger than an illumination wavelength used by a lithography tool, wherein the third pitch is smaller than the illumination wavelength used by the lithography tool.

22. A target design comprising:
a plurality of structures including a plurality of elements, wherein the plurality of structures are arranged based on a first pitch and a second pitch in a first direction along a first axis, wherein the plurality of elements are arranged based on a third pitch in a second direction along a second axis substantially perpendicular to the first axis,
wherein the first pitch includes a spatial distance between adjacent structures of the plurality of structures, wherein the second pitch includes a spatial distance between non-adjacent structures of the plurality of structures, wherein the second pitch is larger than the first pitch,
wherein the plurality of elements includes a plurality of focus-insensitive elements arranged in a focus-insensitive pattern, wherein the third pitch includes a spatial distance between adjacent focus-insensitive elements of the plurality of focus-insensitive elements,
wherein the plurality of elements includes a plurality of focus-sensitive elements arranged in a focus-sensitive pattern, wherein a set of the plurality of focus-sensitive elements is positioned between adjacent focus-insensitive elements of the plurality of focus-insensitive elements,
wherein the set of the plurality of focus-sensitive elements positioned between adjacent focus-insensitive elements of the plurality of focus-insensitive elements are arranged based on a fourth pitch, wherein the fourth pitch includes a spatial distance smaller than the spatial distance of the third pitch.

* * * * *